(12) United States Patent
Tegg et al.

(10) Patent No.: US 11,672,947 B2
(45) Date of Patent: Jun. 13, 2023

(54) LUMEN MANAGEMENT CATHETER

(71) Applicant: St. Jude Medical, Cardiology Division, Inc., St. Paul, MN (US)

(72) Inventors: Troy T. Tegg, Elk River, MN (US); Jacob J. Daly, Blaine, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 219 days.

(21) Appl. No.: 16/203,129

(22) Filed: Nov. 28, 2018

(65) Prior Publication Data

US 2019/0160256 A1 May 30, 2019

Related U.S. Application Data

(60) Provisional application No. 62/743,389, filed on Oct. 9, 2018, provisional application No. 62/591,278, filed on Nov. 28, 2017.

(51) Int. Cl.
*A61M 25/00* (2006.01)
*A61M 25/01* (2006.01)
(Continued)

(52) U.S. Cl.
CPC .... *A61M 25/0026* (2013.01); *A61M 25/0009* (2013.01); *A61M 25/0032* (2013.01); *A61M 25/0144* (2013.01); *A61M 25/10* (2013.01); *A61B 18/1492* (2013.01); *A61B 34/25* (2016.02); *A61B 2017/00327* (2013.01); *A61B 2017/00867* (2013.01); *A61B 2018/00357* (2013.01); *A61B 2018/00577* (2013.01); *A61B 2018/00791* (2013.01); *A61B 2018/00821* (2013.01); *A61B 2018/0212* (2013.01); *A61B 2018/1405* (2013.01);
(Continued)

(58) Field of Classification Search
CPC .......... A61M 25/0026; A61M 25/0032; A61M 25/0074; A61M 25/0144; A61M 25/0045; A61M 25/0054; A61M 25/0147; A61M 2025/0035; A61M 2025/0036; A61M 2025/0037; A61B 2017/3449
See application file for complete search history.

(56) References Cited

U.S. PATENT DOCUMENTS 4,754,752 A 7/1988 Ginsburg et al.
4,790,817 A 12/1988 Luther
(Continued)

FOREIGN PATENT DOCUMENTS

CN 102727987 A 10/2012
CN 101927053 B 1/2015
(Continued)

*Primary Examiner* — Nathan R Price
*Assistant Examiner* — Justin L Zamory
(74) *Attorney, Agent, or Firm* — Kilpatrick Townsend & Stockton LLP

(57) ABSTRACT

An elongate medical device comprising a first lumen, wherein a cross-sectional shape of the first lumen comprises a peanut shape, and a plurality of second lumens, wherein the plurality of second lumens are proximate the first lumen, wherein the first lumen comprises a lumen liner that conforms to the cross-sectional shape of the first lumen, wherein the lumen liner comprises a first material and the elongate medical device comprises a second material, where the first material is different from the second material.

14 Claims, 9 Drawing Sheets

(51) Int. Cl.
*A61B 18/14* (2006.01)
*A61M 25/10* (2013.01)
*A61B 18/02* (2006.01)
*A61B 18/00* (2006.01)
*A61B 34/00* (2016.01)
*A61B 17/00* (2006.01)

(52) U.S. Cl.
CPC .... *A61B 2218/002* (2013.01); *A61M 25/0045* (2013.01); *A61M 25/0054* (2013.01); *A61M 25/0136* (2013.01); *A61M 25/0141* (2013.01); *A61M 25/0147* (2013.01); *A61M 2025/0035* (2013.01); *A61M 2025/0036* (2013.01); *A61M 2025/0037* (2013.01); *A61M 2025/0046* (2013.01); *A61M 2025/0063* (2013.01)

(56) References Cited

U.S. PATENT DOCUMENTS

| | | |
|---|---|---|
| 4,989,608 A | 2/1991 | Ratner |
| 5,007,898 A | 4/1991 | Rosenbluth et al. |
| 5,190,050 A * | 3/1993 | Nitzsche ........... A61M 25/0136 600/585 |
| 5,224,939 A | 7/1993 | Holman et al. |
| 5,374,245 A | 12/1994 | Mahurkar |
| 5,380,301 A | 1/1995 | Prichard et al. |
| 5,400,783 A | 3/1995 | Pomeranz et al. |
| 5,456,254 A | 10/1995 | Pietroski et al. |
| 5,562,652 A | 10/1996 | Davis |
| 5,626,136 A | 5/1997 | Webster, Jr. |
| 5,715,817 A | 2/1998 | Stevens-Wright et al. |
| 5,715,832 A | 2/1998 | Koblish et al. |
| 5,826,576 A | 10/1998 | West |
| 5,827,278 A | 10/1998 | Webster, Jr. |
| 5,833,650 A | 11/1998 | Imran |
| 5,876,373 A | 3/1999 | Giba et al. |
| 5,987,344 A | 11/1999 | West |
| 6,004,310 A | 12/1999 | Bardsley et al. |
| 6,074,379 A | 6/2000 | Prichard |
| 6,102,929 A | 8/2000 | Conway et al. |
| 6,273,404 B1 | 8/2001 | Holman et al. |
| 6,454,997 B1 * | 9/2002 | Divino, Jr. .......... A61M 1/3621 128/DIG. 3 |
| 6,491,681 B1 | 12/2002 | Kunis et al. |
| 6,524,302 B2 | 2/2003 | Kelley |
| 6,527,753 B2 | 3/2003 | Sekine et al. |
| 6,554,794 B1 | 4/2003 | Mueller et al. |
| 6,890,329 B2 | 5/2005 | Carroll et al. |
| 7,004,937 B2 | 2/2006 | Lentz et al. |
| 7,087,064 B1 * | 8/2006 | Hyde ............... A61B 17/00234 606/139 |
| 7,214,220 B2 | 5/2007 | McGlinch et al. |
| 7,217,256 B2 | 5/2007 | Di Palma |
| 7,263,397 B2 | 8/2007 | Hauck et al. |
| 7,386,339 B2 | 6/2008 | Strommer et al. |
| 7,608,063 B2 | 10/2009 | Le et al. |
| 7,625,365 B2 | 12/2009 | McGlinch et al. |
| 7,666,204 B2 | 2/2010 | Thornton et al. |
| 7,959,601 B2 | 6/2011 | McDaniel et al. |
| 7,985,215 B2 | 7/2011 | Guo et al. |
| 8,103,327 B2 | 1/2012 | Harlev et al. |
| 8,137,321 B2 | 3/2012 | Argentine |
| 8,221,390 B2 | 7/2012 | Pal et al. |
| 8,273,016 B2 | 9/2012 | O'Sullivan |
| 8,376,990 B2 | 2/2013 | Ponzi et al. |
| 8,444,637 B2 | 5/2013 | Podmore et al. |
| 8,447,377 B2 | 5/2013 | Harlev et al. |
| 8,608,703 B2 | 12/2013 | Riles et al. |
| 8,649,880 B1 | 2/2014 | Parker, Jr. |
| 8,700,120 B2 | 4/2014 | Koblish |
| 8,706,193 B2 | 4/2014 | Govari et al. |
| 8,755,861 B2 | 6/2014 | Harlev et al. |
| 8,777,929 B2 | 7/2014 | Schneider et al. |
| 8,792,962 B2 | 7/2014 | Esguerra et al. |
| 8,814,824 B2 | 8/2014 | Kauphusman et al. |
| 8,814,825 B2 | 8/2014 | Tegg et al. |
| 8,882,705 B2 | 11/2014 | McDaniel et al. |
| 8,894,610 B2 | 11/2014 | Macnamara et al. |
| 8,996,091 B2 | 3/2015 | de la Rama et al. |
| 9,017,308 B2 | 4/2015 | Klisch et al. |
| 9,033,917 B2 | 5/2015 | Magana et al. |
| 9,050,010 B2 | 6/2015 | Bui et al. |
| 9,101,733 B2 | 8/2015 | McDaniel |
| 9,204,929 B2 | 12/2015 | Solis |
| 9,216,056 B2 | 12/2015 | Datta et al. |
| 9,247,990 B2 | 2/2016 | Kauphusman et al. |
| 9,314,586 B2 | 4/2016 | Chesnin |
| 9,326,815 B2 | 5/2016 | Watson |
| 9,339,631 B2 | 5/2016 | Graham et al. |
| 9,433,751 B2 | 9/2016 | Ponzi et al. |
| 9,433,752 B2 | 9/2016 | Jimenez et al. |
| 9,468,495 B2 | 10/2016 | Kunis et al. |
| 9,486,280 B2 | 11/2016 | Koblish et al. |
| 9,486,282 B2 | 11/2016 | Solis |
| 9,539,413 B2 | 1/2017 | Ogle |
| 9,649,158 B2 | 5/2017 | Datta et al. |
| 9,687,166 B2 | 6/2017 | Subramaniam et al. |
| 9,693,733 B2 | 7/2017 | Altmann et al. |
| 9,693,820 B2 | 7/2017 | Potter et al. |
| 9,694,159 B2 | 7/2017 | Schneider et al. |
| 9,694,161 B2 | 7/2017 | Selkee |
| 9,788,895 B2 | 10/2017 | Solis |
| 9,820,664 B2 | 11/2017 | Hoitink et al. |
| 9,844,645 B2 | 12/2017 | Pai et al. |
| 9,848,795 B2 | 12/2017 | Marecki et al. |
| 9,919,132 B2 | 3/2018 | Tegg et al. |
| 9,949,656 B2 | 4/2018 | Wu et al. |
| 9,986,949 B2 | 6/2018 | Govari et al. |
| 10,004,877 B2 | 6/2018 | Tegg |
| 10,034,637 B2 | 7/2018 | Harlev et al. |
| 10,052,457 B2 | 8/2018 | Nguyen et al. |
| 10,065,019 B2 | 9/2018 | Hamuro et al. |
| 10,099,036 B2 | 10/2018 | Heideman et al. |
| 10,118,022 B2 | 11/2018 | Helgeson et al. |
| 10,143,394 B2 | 12/2018 | Solis |
| 10,322,261 B2 | 6/2019 | Pai et al. |
| 10,362,952 B2 | 7/2019 | Basu et al. |
| 10,362,954 B2 | 7/2019 | de la Rama et al. |
| 10,376,170 B2 | 8/2019 | Quinn et al. |
| 10,384,036 B2 | 8/2019 | Romoscanu |
| 10,398,500 B2 | 9/2019 | Huszar et al. |
| 10,478,325 B2 | 11/2019 | Syed |
| 10,506,938 B2 | 12/2019 | Wu et al. |
| 10,537,259 B2 | 1/2020 | Wu et al. |
| 10,542,899 B2 | 1/2020 | Wu et al. |
| 10,556,091 B2 | 2/2020 | Truhler et al. |
| 10,575,742 B2 | 3/2020 | Wu et al. |
| 10,575,745 B2 | 3/2020 | Solis |
| 10,595,738 B2 | 3/2020 | Sterrett et al. |
| 10,595,740 B2 | 3/2020 | Hoitink et al. |
| 10,602,948 B2 | 3/2020 | Wu et al. |
| 10,646,692 B2 | 5/2020 | Tegg et al. |
| 10,653,423 B2 | 5/2020 | Starnes |
| 10,702,677 B2 | 7/2020 | Okamura et al. |
| 10,737,060 B2 | 8/2020 | Gupta et al. |
| 10,835,712 B2 | 11/2020 | Wada |
| 10,842,990 B2 | 11/2020 | de la Rama et al. |
| 10,857,349 B2 | 12/2020 | de la Rama et al. |
| 10,869,992 B2 | 12/2020 | Pai et al. |
| 10,898,685 B2 | 1/2021 | Tegg |
| 10,912,925 B2 | 2/2021 | Houck |
| 10,953,196 B2 | 3/2021 | Raab et al. |
| 10,959,636 B2 | 3/2021 | Dahlen et al. |
| 10,966,623 B2 | 4/2021 | Wu et al. |
| 10,966,753 B2 | 4/2021 | Coyle et al. |
| 10,967,150 B2 | 4/2021 | Helgeson et al. |
| 10,987,045 B2 | 4/2021 | Basu et al. |
| 11,033,715 B2 | 6/2021 | Beeckler et al. |
| 11,039,772 B2 | 6/2021 | Wu et al. |
| 11,039,773 B2 | 6/2021 | Sterrett et al. |
| 11,083,400 B2 | 8/2021 | Hoitink et al. |
| 11,116,436 B2 | 9/2021 | Wu et al. |
| 11,116,476 B2 | 9/2021 | Buesseler et al. |

(56) References Cited

U.S. PATENT DOCUMENTS

| | | |
|---|---|---|
| 11,141,568 B2 | 10/2021 | Hsueh et al. |
| 11,160,482 B2 | 11/2021 | Solis |
| 11,172,858 B2 | 11/2021 | Olson et al. |
| 11,272,886 B2 | 3/2022 | Harlev et al. |
| 2002/0165484 A1 | 11/2002 | Bowe et al. |
| 2004/0193032 A1 | 9/2004 | Mogul |
| 2005/0070880 A1 | 3/2005 | Varma et al. |
| 2005/0107736 A1* | 5/2005 | Landman ............ A61M 31/00 604/93.01 |
| 2006/0020256 A1* | 1/2006 | Bell .................. A61M 25/0045 604/523 |
| 2006/0161100 A1 | 7/2006 | Hamboly |
| 2007/0219441 A1* | 9/2007 | Carlin ................ A61M 25/007 600/347 |
| 2009/0247868 A1* | 10/2009 | Chesnin ............ A61M 25/0032 600/435 |
| 2012/0253161 A1 | 10/2012 | Harlev et al. |
| 2012/0316436 A1* | 12/2012 | Lentz ................ A61M 25/0043 600/435 |
| 2013/0296781 A1* | 11/2013 | Tegg ................ A61M 25/0026 604/95.04 |
| 2014/0100639 A1 | 4/2014 | Lee et al. |
| 2014/0323964 A1* | 10/2014 | Leeflang .......... A61M 25/0045 604/95.04 |
| 2015/0119911 A1 | 4/2015 | Mckenzie |
| 2015/0320971 A1 | 11/2015 | Leeflang et al. |
| 2015/0366508 A1 | 12/2015 | Chou et al. |
| 2016/0213423 A1 | 7/2016 | Kauphusman et al. |
| 2016/0278851 A1 | 9/2016 | Mannion et al. |
| 2016/0331933 A1 | 11/2016 | Knutsen |
| 2016/0346040 A1 | 12/2016 | Hall et al. |
| 2017/0281268 A1 | 10/2017 | Tran et al. |
| 2017/0319269 A1 | 11/2017 | Oliverius et al. |
| 2017/0367756 A1 | 12/2017 | Sliwa et al. |
| 2018/0042667 A1 | 2/2018 | Pappone et al. |
| 2018/0085064 A1 | 3/2018 | Auerbach et al. |
| 2018/0161093 A1 | 6/2018 | Basu et al. |
| 2018/0229030 A1 | 8/2018 | Dubuclet et al. |
| 2018/0369574 A1 | 12/2018 | Dubuclet et al. |
| 2019/0009052 A1 | 1/2019 | Oliverius et al. |
| 2019/0125378 A1 | 5/2019 | Shelton, IV et al. |
| 2019/0192826 A1 | 6/2019 | Wada |
| 2020/0121894 A1 | 4/2020 | Prabhu et al. |
| 2020/0138378 A1 | 5/2020 | de la Rama et al. |
| 2020/0214635 A1 | 7/2020 | Dahlen et al. |
| 2020/0253496 A1 | 8/2020 | Deno et al. |
| 2020/0405166 A1 | 12/2020 | Wu et al. |
| 2021/0145342 A1 | 5/2021 | Wang |
| 2021/0187246 A1 | 6/2021 | Houck |
| 2021/0204871 A1 | 7/2021 | Goedeke et al. |
| 2021/0268234 A1 | 9/2021 | Helgeson et al. |
| 2021/0298656 A1 | 9/2021 | Wu et al. |
| 2021/0361216 A1 | 11/2021 | Hoitink et al. |
| 2021/0401345 A1 | 12/2021 | Wu et al. |
| 2022/0023594 A1 | 1/2022 | Pai |
| 2022/0054066 A1 | 2/2022 | Solis |
| 2022/0061727 A1 | 3/2022 | Olson et al. |

FOREIGN PATENT DOCUMENTS

| | | |
|---|---|---|
| CN | 103157168 B | 4/2015 |
| CN | 106859765 A | 6/2017 |
| CN | 107184271 A | 9/2017 |
| CN | 206880930 U | 1/2018 |
| CN | 104958824 B | 12/2018 |
| CN | 104434083 B | 4/2019 |
| CN | 104968261 B | 5/2019 |
| CN | 105592778 B | 7/2019 |
| CN | 110536646 A | 12/2019 |
| CN | 111225627 A | 6/2020 |
| CN | 111432739 A | 7/2020 |
| CN | 111657866 A | 9/2020 |
| CN | 106264715 B | 11/2020 |
| CN | 106264716 B | 11/2020 |
| CN | 106308790 B | 6/2021 |
| CN | 107529958 B | 7/2021 |
| CN | 109310469 B | 7/2021 |
| CN | 109641121 B | 9/2021 |
| CN | 109952123 B | 9/2021 |
| CN | 110545874 B | 9/2021 |
| CN | 110559544 B | 9/2021 |
| CN | 113425304 A | 9/2021 |
| CN | 105615994 B | 10/2021 |
| CN | 109963610 B | 11/2021 |
| CN | 108289709 B | 3/2022 |
| DE | 102016107107 A1 | 10/2017 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2604306 B1 | 1/2014 |
| EP | 2915555 A1 | 9/2015 |
| EP | 1968679 B1 | 9/2016 |
| EP | 2241279 B1 | 9/2016 |
| EP | 3115076 A4 | 10/2017 |
| EP | 3117863 A4 | 10/2017 |
| EP | 3111871 B1 | 3/2018 |
| EP | 3111872 B1 | 4/2018 |
| EP | 3057488 B1 | 5/2018 |
| EP | 2848226 B1 | 7/2018 |
| EP | 3363397 A1 | 8/2018 |
| EP | 3391928 A1 | 10/2018 |
| EP | 3122276 B1 | 11/2018 |
| EP | 3398549 A1 | 11/2018 |
| EP | 1759668 B1 | 12/2018 |
| EP | 3037122 B1 | 12/2018 |
| EP | 2234537 B1 | 1/2019 |
| EP | 2569040 B1 | 2/2019 |
| EP | 3023052 B1 | 3/2019 |
| EP | 3466363 A1 | 4/2019 |
| EP | 2550989 B1 | 6/2019 |
| EP | 3512589 A1 | 7/2019 |
| EP | 3512590 A1 | 7/2019 |
| EP | 3527125 A1 | 8/2019 |
| EP | 3531903 A1 | 9/2019 |
| EP | 3434218 B1 | 2/2020 |
| EP | 2908723 B1 | 3/2020 |
| EP | 3114987 B1 | 8/2020 |
| EP | 3178516 B1 | 9/2020 |
| EP | 3738508 A1 | 11/2020 |
| EP | 3738509 A1 | 11/2020 |
| EP | 3340916 B1 | 12/2020 |
| EP | 3579908 B1 | 12/2020 |
| EP | 3750475 A1 | 12/2020 |
| EP | 2155301 B1 | 4/2021 |
| EP | 3432820 B1 | 4/2021 |
| EP | 3476331 B1 | 5/2021 |
| EP | 3579758 B1 | 5/2021 |
| EP | 2809254 B1 | 6/2021 |
| EP | 3508245 B1 | 7/2021 |
| EP | 3858277 A1 | 8/2021 |
| EP | 3892221 A1 | 10/2021 |
| EP | 3932343 A4 | 1/2022 |
| EP | 3791820 B9 | 4/2022 |
| JP | 4545384 B2 | 7/2010 |
| JP | 4887810 B2 | 2/2012 |
| JP | 4940332 B2 | 3/2012 |
| JP | 2012055602 A | 3/2012 |
| JP | 2012200509 A | 10/2012 |
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5550150 B2 | 5/2014 |
| JP | 5762697 B2 | 6/2015 |
| JP | 5856712 B2 | 2/2016 |
| JP | 5908270 B2 | 4/2016 |
| JP | 5944331 B2 | 7/2016 |
| JP | 6050522 B2 | 12/2016 |

(56) References Cited

FOREIGN PATENT DOCUMENTS

| | | |
|---|---|---|
| JP | 2017051211 A | 3/2017 |
| JP | 2017104552 A | 6/2017 |
| JP | 6246742 B2 | 12/2017 |
| JP | 6342524 B2 | 6/2018 |
| JP | 6434495 B2 | 12/2018 |
| JP | 6445509 B2 | 12/2018 |
| JP | 6445742 B1 | 12/2018 |
| JP | 6466114 B2 | 2/2019 |
| JP | 6515084 B2 | 4/2019 |
| JP | 6528010 B1 | 5/2019 |
| JP | 6655655 B2 | 2/2020 |
| JP | 6776021 B2 | 10/2020 |
| JP | 6776025 B2 | 10/2020 |
| JP | 6786275 B2 | 11/2020 |
| JP | 6821812 B2 | 1/2021 |
| JP | 2021007772 A | 1/2021 |
| JP | 2021501011 A | 1/2021 |
| JP | 6843502 B2 | 3/2021 |
| JP | 6894004 B2 | 6/2021 |
| JP | 6920312 B2 | 8/2021 |
| JP | 6926306 B2 | 8/2021 |
| JP | 6932484 B2 | 8/2021 |
| JP | 6936872 B2 | 9/2021 |
| JP | 6980386 B2 | 11/2021 |
| JP | 2022020838 A | 2/2022 |
| WO | 9843530 A1 | 10/1998 |
| WO | 0168178 A1 | 9/2001 |
| WO | 2008091197 A1 | 7/2008 |
| WO | 2009085652 A1 | 7/2009 |
| WO | 2013/169815 A1 | 11/2013 |
| WO | 2014/170782 A1 | 10/2014 |
| WO | 2017098198 A1 | 6/2017 |
| WO | 2018053148 A1 | 3/2018 |
| WO | 2018053164 A1 | 3/2018 |
| WO | 2018136741 A1 | 7/2018 |
| WO | 2019108661 A1 | 6/2019 |
| WO | 2019108664 A2 | 6/2019 |

\* cited by examiner

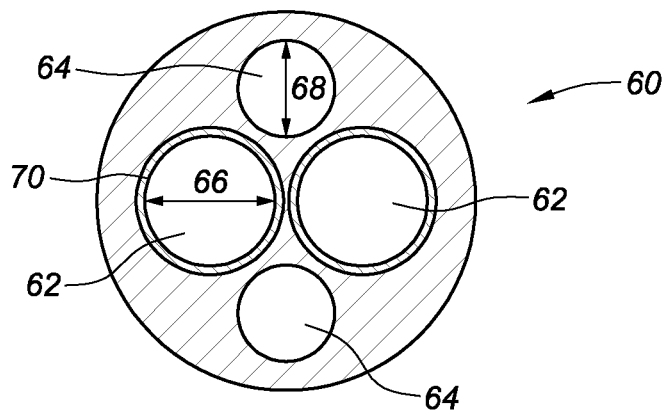
FIG. 3
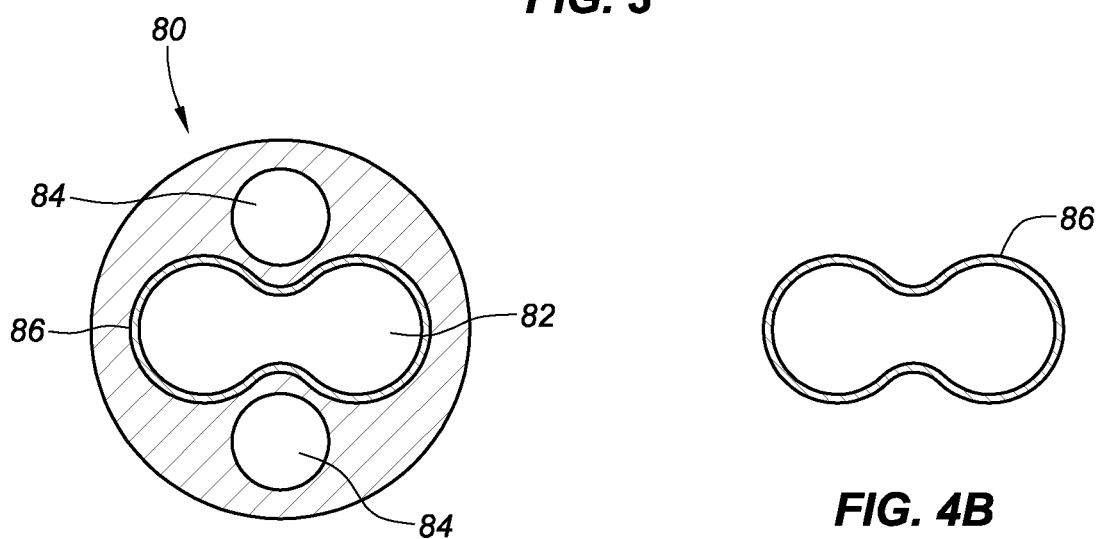
FIG. 4A
FIG. 4B
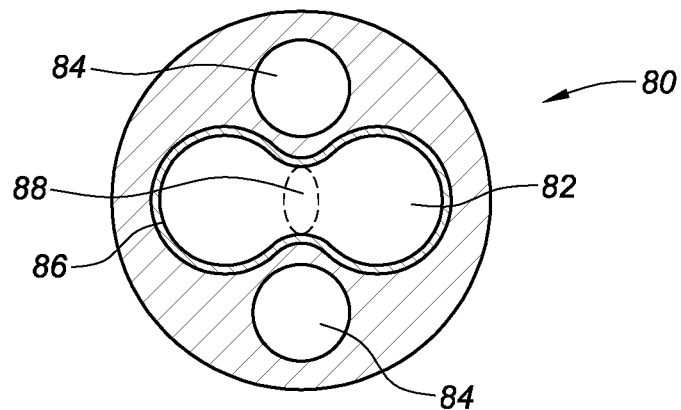
FIG. 5

LUMEN MANAGEMENT CATHETER

CROSS-REFERENCE TO RELATED APPLICATIONS

This application claims the benefit of U.S. provisional patent application No. 62/591,278, filed on 28 Nov. 2017 (the '278 application) and this application claims the benefit of U.S. provisional patent application No. 62/743,389, filed on 9 Oct. 2018 (the '389 application). The '278 application and the '389 application are both hereby incorporated by reference as though fully set forth herein.

BACKGROUND a. Field

This disclosure relates to systems and apparatuses for catheter-based cardiac electrophysiology mapping and therapy. In particular, the instant disclosure relates to lumen management in catheters for mapping and therapy.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other therapies and/or treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

To position a catheter at a desired site within the body, some type of navigation may be used, such as using mechanical steering features incorporated into the catheter (or an introducer). In some examples, medical personnel may manually manipulate and/or operate the catheter using the mechanical steering features.

In order to facilitate the advancement of catheters through a patient's vasculature, a navigating system may be used. Such navigating systems may include, for example, electric-field-based positioning and navigating systems that are able to determine the position and orientation of the catheter (and similar devices) within the body and map features of the body. Various therapies can be delivered by the catheter to tissue with varied shapes and sizes. To better accommodate various sensors and devices at a distal end portion of a catheter used to map features of the body, evaluate sufficient contact with the tissue for therapy and/or provide therapy to the tissue, it can be important to have multiple sensors coupled with flexible circuits and wires in addition to other lumens inside a catheter. The ability to manage the various wires and flexible circuits is necessary to accommodate larger cross-sectional shapes (compared to existing catheters) of some sensors and flexible circuits the sensors a catheter. It is also desirable to use the elements inside the lumen to assist with maintaining planarity of the catheter when the catheter changes shape during a procedure.

The foregoing discussion is intended only to illustrate the present field and should not be taken as disavowal of claim scope.

BRIEF SUMMARY

The instant disclosure, in at least one embodiment, comprises a first lumen, wherein a cross-sectional shape of the first lumen comprises a peanut shape, and a plurality of second lumens, wherein the plurality of second lumens are proximate the first lumen, wherein the first lumen comprises a lumen liner that conforms to the cross-sectional shape of the first lumen, wherein the lumen liner comprises a first material and the elongate medical device comprises a second material, where the first material is different from the second material.

Another embodiment, comprises a method of forming a lumen liner, comprising inserting one or more mandrels into a tube, aligning the tube in a mold assembly, wherein the mold assembly comprises a mold cross-section that corresponds to a lumen liner cross-section, compressing the mold assembly around the tube and the one or more mandrels, heating the mold assembly for a first period of time, cooling the mold assembly for a second period of time, uncompressing the mold assembly, removing the lumen liner from the mold assembly, and removing the mandrels from the lumen liner.

BRIEF DESCRIPTION OF THE DRAWINGS

FIG. 2 generally illustrates a deflectable electrophysiology catheter FIG. 3 is a cross-sectional view of a current catheter design including a plurality of individual lumens for use with a catheter, in accordance with embodiments of the present disclosure.

FIG. 4A is a cross-sectional view of a catheter comprising a plurality of lumens for use with a catheter, in accordance with embodiments of the present disclosure.

FIG. 4B is a cross-sectional view of the lumen liner of FIG. 4A, in accordance with embodiments of the present disclosure.

FIG. 5 is a cross-sectional view of the catheter of FIG. 3 showing additional lumen space of the configuration compared to the lumen space in the catheter of FIG. 2, in accordance with embodiments of the present disclosure.

DETAILED DESCRIPTION OF EMBODIMENTS

Figure 1:
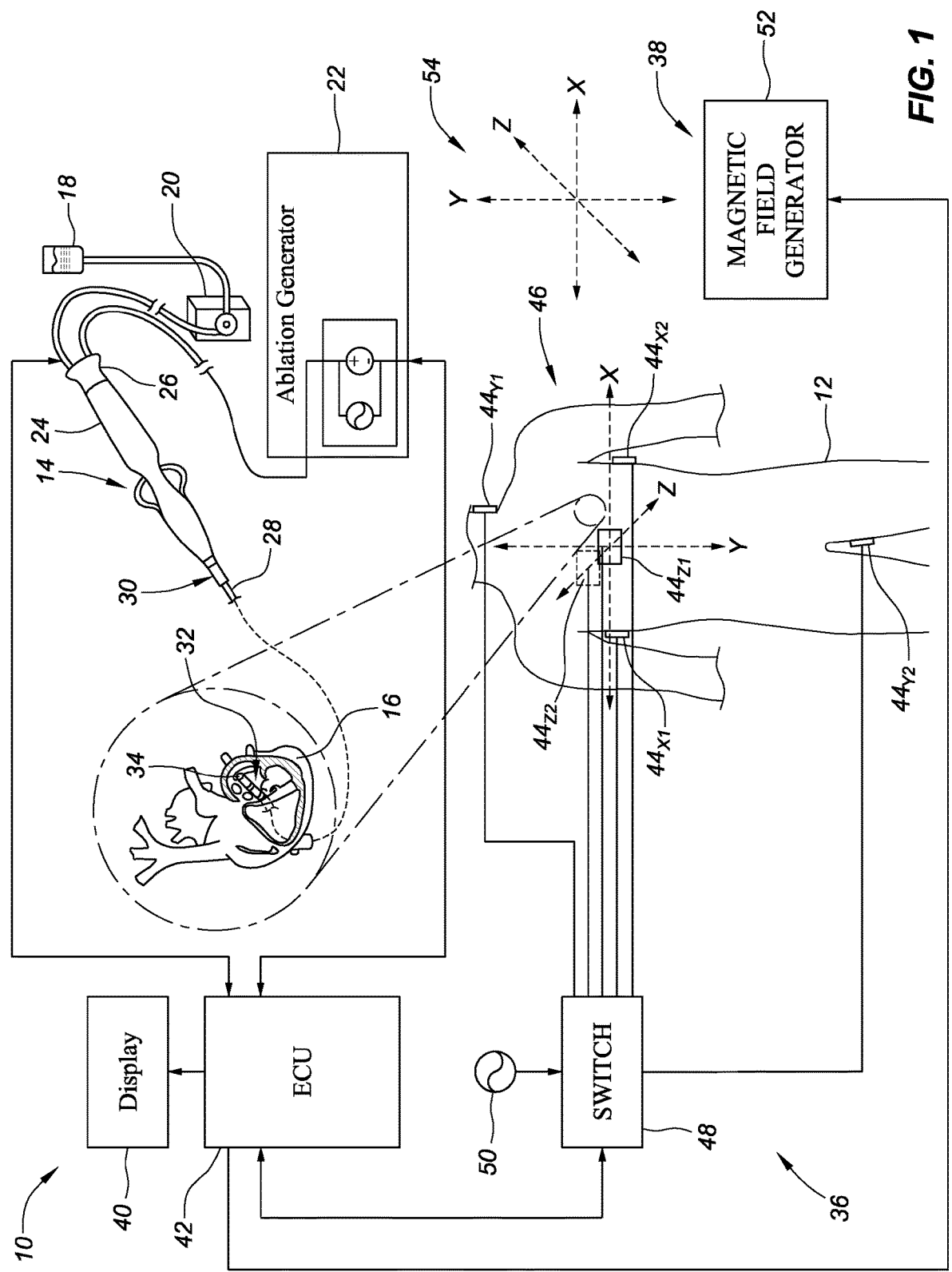
FIG. 1 is a system diagram showing a medical device and a medical positioning system, in accordance with embodiments of the present disclosure.

Referring now to the figures, in which like reference numerals refer to the same or similar features in the various views, FIG. 1 illustrates one embodiment of a system 10 for navigating a medical device within a body 12. In the illustrated embodiment, the medical device comprises a catheter 14 that is shown schematically entering a heart that has been exploded away from the body 12. The catheter 14, in this embodiment, is depicted as an irrigated radiofrequency (RF) ablation catheter for use in the treatment of cardiac tissue 16 in the body 12. It should be understood, however, that the system 10 may find application in connection with a wide variety of medical devices used within the body 12 for diagnosis or treatment. For example, the system 10 may be used to navigate, for example, an electrophysiological catheter, a mapping catheter, an intracardiac echocardiography (ICE) catheter, or an ablation catheter using a different type of ablation energy (e.g., cryoablation, ultrasound, etc.). Further, it should be understood that the system 10 may be used to navigate medical devices used in the diagnosis or treatment of portions of the body 12 other than cardiac tissue 16. Further description of the systems and components are contained in U.S. patent application Ser. No. 13/839,963 filed on 15 Mar. 2013, which is hereby incorporated by reference in its entirety as though fully set forth herein.

Referring still to FIG. 1, the ablation catheter 14 is connected to a fluid source 18 for delivering a biocompatible irrigation fluid such as saline through a pump 20, which may comprise, for example, a fixed rate roller pump or variable volume syringe pump with a gravity feed supply from fluid source 18 as shown. The catheter 14 is also electrically connected to an ablation generator 22 for delivery of RF energy. The catheter 14 may include a handle 24; a cable connector or interface 26 at a proximal end of the handle 24; and a shaft 28 having a proximal end 30, a distal end 32, and one or more electrodes 34. The connector 26 provides mechanical, fluid, and electrical connections for conduits or cables extending from the pump 20 and the ablation generator 22. The catheter 14 may also include other conventional components not illustrated herein such as a temperature sensor, additional electrodes, and corresponding conductors or leads.

The handle 24 provides a location for the physician to hold the catheter 14 and may further provide means for steering or guiding the shaft 28 within the body 12. For example, the handle 24 may include means to change the length of one or more pull wires extending through the catheter 14 from the handle 24 to the distal end 32 of shaft 28. The construction of the handle 24 may vary.

The shaft 28 may be made from conventional materials such as polyurethane and may define one or more lumens configured to house and/or transport electrical conductors, fluids, or surgical tools. The shaft 28 may be introduced into a blood vessel or other structure within the body 12 through a conventional introducer. The shaft 28 may then be steered or guided through the body 12 to a desired location such as the tissue 16 using guide wires or pull wires or other means known in the art including remote control guidance systems. The shaft 28 may also permit transport, delivery, and/or removal of fluids (including irrigation fluids and bodily fluids), medicines, and/or surgical tools or instruments. It should be noted that any number of methods can be used to introduce the shaft 28 to areas within the body 12. This can include introducers, sheaths, guide sheaths, guide members, guide wires, or other similar devices. For ease of discussion, the term introducer will be used throughout.

The system 10 may include an electric-field-based positioning system 36, a magnetic-field-based positioning system 38, a display 40, and an electronic control unit (ECU) 42 (e.g., a processor). Each of the exemplary system components is described further below.

The electric-field-based positioning system 36 and the magnetic-field-based positioning system 38 are provided to determine the position and orientation of the catheter 14 and similar devices within the body 12. The position and orientation of the catheter 14 and similar devices within the body 12 can be determined by the system 36 and/or the system 38. The system 36 may comprise, for example, the EnSite™ NavX™ system sold by St. Jude Medical, Inc. of St. Paul, Minn., and described in, for example, U.S. Pat. No. 7,263,397 titled "Method and Apparatus for Catheter Navigation and Location Mapping in the Heart," the entire disclosure of which is hereby incorporated by reference as though fully set forth herein. The systems 36 and 38 may comprise, for example, the EnSite Precision™ system sold by St. Jude Medical, Inc., of St. Paul, Minn. The system 36 operates based upon the principle that when low amplitude electrical signals are passed through the thorax, the body 12 acts as a voltage divider (or potentiometer or rheostat) such that the electrical potential or field strength measured at one or more electrodes 34 on the catheter 14 may be used to determine the position of the electrodes, and, therefore, of the catheter 14, relative to a pair of external patch electrodes using Ohm's law and the relative location of a reference electrode (e.g., in the coronary sinus).

In the configuration is shown in FIG. 1, the electric-field-based positioning system 36 further includes three pairs of patch electrodes 44, which are provided to generate electrical signals used in determining the position of the catheter 14 within a three-dimensional coordinate system 46. The electrodes 44 may also be used to generate EP data regarding the tissue 16. To create axes-specific electric fields within body 12, the patch electrodes are placed on opposed surfaces of the body 12 (e.g., chest and back, left and right sides of the thorax, and neck and leg) and form generally orthogonal x, y, and z axes. A reference electrode/patch (not shown) is typically placed near the stomach and provides a reference value and acts as the origin of the coordinate system 46 for the navigation system.

In accordance with this exemplary system 36 as depicted in FIG. 1, the patch electrodes include right side patch $44_{X1}$, left side patch $44_{X2}$, neck patch $44_{Y1}$, leg patch $44_{Y2}$, chest patch $44_{Z1}$, and back patch $44_{Z2}$; and each patch electrode is connected to a switch 48 (e.g., a multiplex switch) and a signal generator 50. The patch electrodes $44_{X1}$, $44_{X2}$ are placed along a first (x) axis; the patch electrodes $44_{Y1}$, $44_{Y2}$ are placed along a second (y) axis, and the patch electrodes $44_{Z1}$, $44_{Z2}$ are placed along a third (z) axis. Sinusoidal currents are driven through each pair of patch electrodes, and voltage measurements for one or more position sensors (e.g., ring electrodes 34 or a tip electrode located near the distal end 32 of catheter shaft 28) associated with the catheter 14 are obtained. The measured voltages are a function of the distance of the position sensors from the patch electrodes. The measured voltages are compared to the potential at the reference electrode and a position of the position sensors within the coordinate system 46 of the navigation system is determined.

The magnetic-field-based positioning system 38 in this exemplary embodiment employs magnetic fields to detect the position and orientation of the catheter 14 within the body 12. The system 38 may include the GMPS system made available by MediGuide, Ltd. and generally shown and described in, for example, U.S. Pat. No. 7,386,339 titled "Medical Imaging and Navigation System," the entire disclosure of which is hereby incorporated by reference as though fully set forth herein. In such a system, a magnetic field generator 52 may be employed having three orthogonally arranged coils (not shown) to create a magnetic field within the body 12 and to control the strength, orientation, and frequency of the field. The magnetic field generator 52 may be located above or below the patient (e.g., under a patient table) or in another appropriate location. Magnetic fields are generated by the coils and current or voltage measurements for one or more position sensors (not shown) associated with the catheter 14 are obtained. The measured currents or voltages are proportional to the distance of the sensors from the coils, thereby allowing determination of a position of the sensors within a coordinate system 54 of system 38.

The display 40 is provided to convey information to a physician to assist in diagnosis and treatment. The display 40 may comprise one or more conventional computer monitors or other display devices. The display 40 may present a graphical user interface (GUI) to the physician. The GUI may include a variety of information including, for example, an image of the geometry of the tissue 16, electrophysiology data associated with the tissue 16, graphs illustrating voltage levels over time for various electrodes 34, and images of the catheter 14 and other medical devices and related information indicative of the position of the catheter 14 and other devices relative to the tissue 16.

The ECU 42 provides a means for controlling the operation of various components of the system 10, including the catheter 14, the ablation generator 22, and magnetic generator 52 of the magnetic-field-based positioning system 38. The ECU 42 may also provide a means for determining the geometry of the tissue 16, electrophysiology characteristics of the tissue 16, and the position and orientation of the catheter 14 relative to tissue 16 and the body 12. The ECU 42 also provides a means for generating display signals used to control the display 40.

As the catheter 14 moves within the body 12, and within the electric field generated by the electric-field-based positioning system 36, the voltage readings from the electrodes 34 change, thereby indicating the location of catheter 14 within the electric field and within the coordinate system 46 established by the system 36. The ring electrodes 34 communicate position signals to ECU 42 through a conventional interface (not shown).

Figure 2:
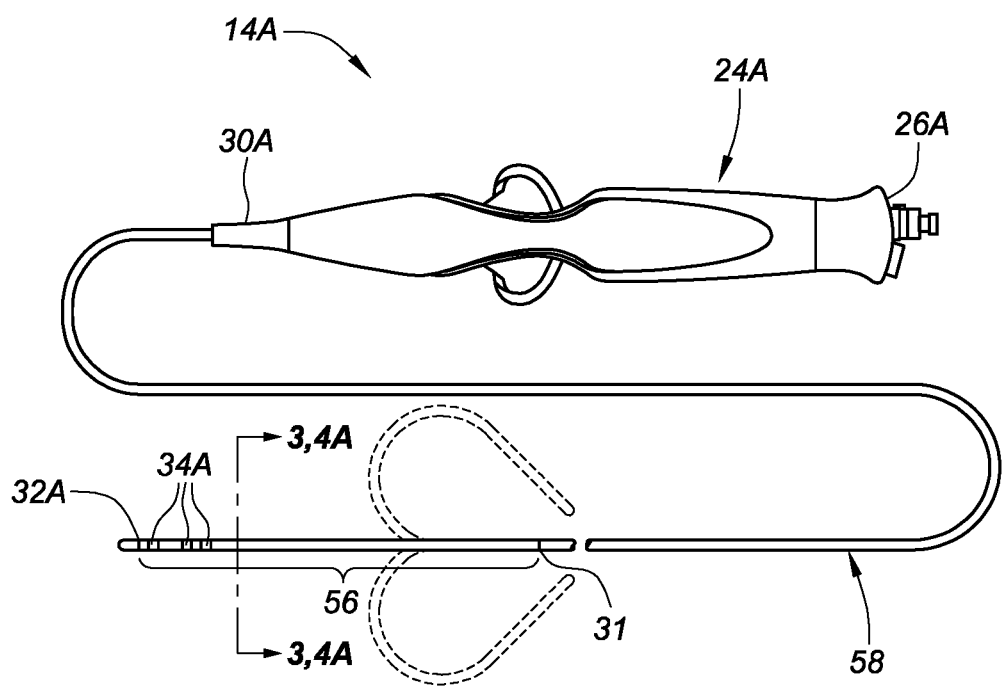
FIG. 2 is a plan view of an elongate medical device with a deflectable shaft section, in accordance with embodiments of the present disclosure.

FIG. 2 is a plan view of an elongate medical device with a deflectable shaft section, in accordance with embodiments of the present disclosure. FIG. 2 generally illustrates a deflectable electrophysiology catheter 14A that comprises a deflectable catheter shaft section 56 and a handle 24A. The deflectable catheter shaft section 56 comprises an elongated body having a distal end 32A and a proximal end 31, where the proximal end 31 is coupled with the proximal catheter shaft section 58. The handle 24A can also include a connector 26A for a cables and/or fluid (see FIG. 1 and related discussion for more information). The distal end 32A of the deflectable catheter shaft section 56 can comprise, for example, electrodes 34A. A distal end 30A of the proximal catheter shaft section 58 is coupled with a handle 24A. Using the handle 24A, the deflectable catheter shaft section 56 can be configured for deflection independent of the proximal catheter shaft section 58. A cross-sectional views of the catheter shaft can be seen in FIGS. 3 and 4A.

FIG. 3 is a cross-sectional view of a current catheter design including a plurality of individual lumens for use with a catheter, in accordance with embodiments of the present disclosure. The catheter 60 can comprise a plurality of first lumens 62 and a plurality of second lumens 64. The plurality of first lumens 62 can be a first lumen diameter 66 and the plurality of second lumens 64 can be a second lumen diameter 68. In some embodiments, the first lumen diameter 66 is larger than the second lumen diameter 68. The plurality of first lumens 62 and the plurality of second lumens 64 can have generally circular cross-sectional shapes.

Each of the plurality of first lumens 62 can include a lumen liner 70. The catheter 60 can comprise a first material. The lumen liner 70 can comprise a second material that is different than the first material. For example, the first material can be polyether block amide (e.g., PEBAX®), nylon, or other suitable materials that are soft and reflowable and the second material can be polyimide, polyether ether keytone (PEEK), polycarbonate, or any suitable material that can be "heat set" to a specific shape (i.e., heated, formed to a shape, and then cooled, while the material allows the new shape to be retained). The second material can provide additional characteristics to the catheter including, for example, additional stiffness (i.e. bending resistance), deflection shape, and planarity control. The lumen liner 70 can fit into each of the plurality of first lumens 62 and can be held in place by friction, adhesive, or other suitable methods.

One or more of the plurality of first lumens 62 can be used to route, for example, fluid, control wires for electrodes, sensors, thermocouples, or other similar items (not shown in FIG. 2). The plurality of second lumens 64 can be used to route, for example, pull wires (not shown in FIG. 2) for deflecting a distal end portion of the catheter 60. The diameter of the plurality of first lumens 62 limits the size of the items/elements that can be routed from a proximal end portion of the catheter 60 to the distal end portion of the catheter 60.

FIG. 4A is a cross-sectional view of a catheter comprising a plurality of lumens for use with a catheter, in accordance with embodiments of the present disclosure. A catheter 80 can comprise a first lumen 82 and a plurality of second lumens 84. The first lumen 82 can include a lumen liner 86. A cross-section of the first lumen 62 can be shaped like a peanut as described in greater detail below. The plurality of second lumens 84 can have a circular cross-section. Other cross-sectional shapes are possible that incorporate including ellipses, ovals, hexagons, etc. where two shapes are adjacent to each other with a section that is joined.

The cross-sectional shape of the first lumen 82 be configured to fit within a catheter (e.g., a generally circular cross-section) and between the plurality of second lumens 84 as shown in FIG. 3. This cross-sectional shape can maximize the size of the first lumen 82 while still maintaining sufficient wall thickness around the exterior of the catheter and between adjacent lumens (e.g., the first lumen 82 and the plurality of second lumens 84).

Benefits of the symmetrical shape of the first lumen 82 can include a larger area (e.g., compared to having two individual lumens (e.g., as shown in FIG. 2) to route wires, flexible circuits, or any other element along the length (or even a portion) of a catheter. The symmetry of the first lumen 82 can also provide for more desirable bending properties of the distal end portion of the catheter. (See FIG. x and related discussion for additional information).

The first lumen 82 can contain one or more tubes (i.e., liners) (not shown in FIG. 4; see FIGS. 6A-B and related discussion for more information) to contain (i.e. containment tubes) or house various elements such as wires for sensors, interactive elements, or similar devices and/or fluid (e.g., saline) to connect from a distal location on the catheter 80 to a proximal location.

FIG. 4B is a cross-sectional view of the lumen liner of FIG. 4A, in accordance with embodiments of the present disclosure. As mentioned above, the lumen liner 86 can be shaped like a peanut (e.g., an hourglass shape, two adjacent circular areas connected, a dumbbell, a modified ellipsoid, a modified ellipsoid with two connected circular areas, an "open" figure-8, etc.). Other ways of describing the cross-sectional shape of the first lumen 82 include, for example, an ellipse with indentations on opposite sides, a shape defined by mathematical formula such as $r=2 \cos 2\theta+4$, or other similar formulae, two circular areas connected by a narrower waist area, etc. Some embodiments of the peanut shape can be symmetrical as shown in FIG. 4A. Other embodiments of the peanut shape can be asymmetrical (not shown; e.g., one circular portion could be larger than the other).

The cross-sectional shape of the lumen liner 86 can be generally described as a shape having three or more distinct areas including a first region (i.e., area, portion, shape) and a second region that are connected by a third region where the first region and the second region are both larger (e.g., by area, or by a width and/or length when viewed as a cross-section) than the third region. The first region and the section region can be the same size (e.g., making the cross-section symmetrical) or the first region and the second region can be different sizes (e.g., making the cross-section asymmetrical). The cross-sectional shape can be the same along a given length or it can vary (e.g., have narrower/wider regions along the length). These variations could be used to, for example, hold or lock in place various elements inside a lumen formed by the lumen liner.

FIG. 5 is a cross-sectional view of the catheter of FIG. 3 showing additional lumen space of the configuration compared to the lumen space in the catheter of FIG. 2, in accordance with embodiments of the present disclosure. The first lumen 82 of the catheter 80 can include an additional area 88 (e.g., compared to having two individual lumens as in FIG. 2) to route wires, flexible circuits, or any other element along the length (or even a portion) of a catheter—including elements that would not otherwise fit within lumens with a smaller cross-section (e.g., the first plurality of lumens 62 in FIG. 2).

FIG. 5A is a cross-sectional view of a catheter with a plurality of lumens, including a plurality of wires, in accordance with embodiments of the present disclosure. A catheter 80A can comprise a first lumen 82A, a lumen liner 86A, one or more flexible circuits 90, a plurality of wires 92, and a plurality of second lumens 84A. In some embodiments, the first lumen 92A can also include a secondary lumen 94 that has smaller cross-section than the cross-section of the lumen liner 86. The secondary lumen 94 can be used as a pathway that is separate from the rest of the first lumen 84. For example, the secondary lumen 94 can be used to transport a fluid from a proximal end portion of the catheter 80 to a distal end portion of the catheter 80.

The catheter 80A can have a deflection plane represented by a line $A_1$-$A_2$. The deflection plane represents the direction that the catheter can bend (e.g., deflect). For example, a user could deflect (for example, using pull wires or other control mechanisms) a distal end portion of the catheter 80A along the line $A_1$-$A_2$ in the direction of A1 or in the direction of A2 (or possible both when, for example, a catheter end portion is bend into an "S" shape). Additionally, the shape of the elements within the first lumen 82A (e.g., the flexible circuit 90) can be configured to promote bending along the bending plane $A_1$-$A_2$ (i.e., provide in plane bending support). For example, the flexible circuit 90 can have a flexible plane $B_1$-$B_2$ represented by the line as shown in FIG. 5A. The flexible circuit 90 can preferentially deflect along the flexible plane $B_1$-$B_2$ (e.g., in the same direction as the deflection plane $A_1$-$A_2$).

The lumen liner 86A can also promote bending along the bending plane $A_1$-$A_2$. The bending support provided by the lumen liner 86A and/or the flexible circuit 90 can help make the bend characteristics of the distal end of the catheter more predictable and more uniform. The ability of the catheter to stay in the bending plane $A_1$-$A_2$ (i.e., maintain planarity), or as close as possible, is desirable for users as it allows for more accurate movement and/or maneuvering of the catheter during a procedure.

In some embodiments (not shown), the flexible circuit 90 can be sized/shaped so a portion of the flexible circuit couples with a portion of the additional area (e.g., the additional area of FIG. 5) of the lumen liner. This can allow the position of the flexible circuit 90 to be fixed (i.e., "locked in") similar to a key fitting into a keyhole. Having the flexible circuit 90 locked in position can assist with the bend characteristics of the deflectable portion of the catheter. As described herein, the flexible circuit 90 can be predisposed to bend more easily in a specific direction (i.e., along a bend plane; see FIGS. 11A-C and related discussion for more information). Having the position of the flexible circuit fixed can minimize and/or eliminate any movement (e.g., slop, variation, etc. outside of a bend plane) of the flexible circuit 90 that could allow a change in the direction of bend that the flexible circuit is predisposed to make when a bending moment is applied to the deflectable portion of the catheter distal end (see FIGS. 11A-C and related discussion for more information).

The plurality of wires 92 can be used to carry signals to/from various sensors, electrodes, thermocouples, and other similar elements at a distal end portion of the catheter 80A and a proximal end portion of the catheter (e.g., to the ablation generator 22, the ECU 42, and the magnetic field generator 52 of FIG. 1). Various wires of the plurality of wires 92 can be electrically coupled with various electrodes (e.g., spot electrodes, ring electrodes, a tip electrode, etc.), sensors (magnetic position sensors, fiber optic sensor fibers, force sensors, strain gauges, strain sensors, biosensors (e.g., sensors capable of converting biological response to an electrical signal), diagnostic sensors, therapy sensors, chemical sensors (e.g., sensors capable of delivery and/or monitoring of drugs/chemicals, etc.), light-emitting sensors, acoustic sensors, thermoelectric elements), thermocouples, and other similar devices.

Figure 6A:
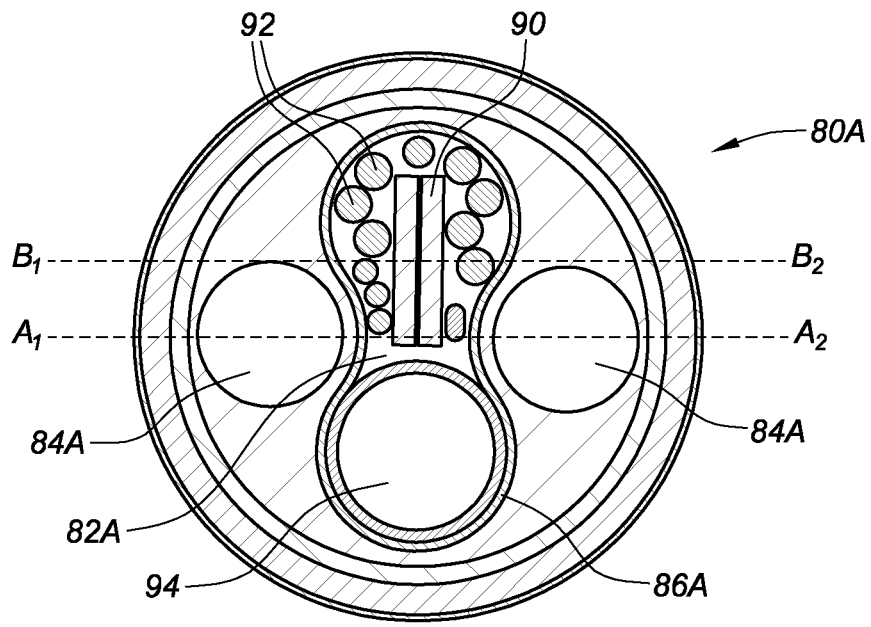
FIG. 6A is a cross-sectional view of a catheter with a plurality of lumens, including a plurality of wires, in accordance with embodiments of the present disclosure.
Figure 6B:
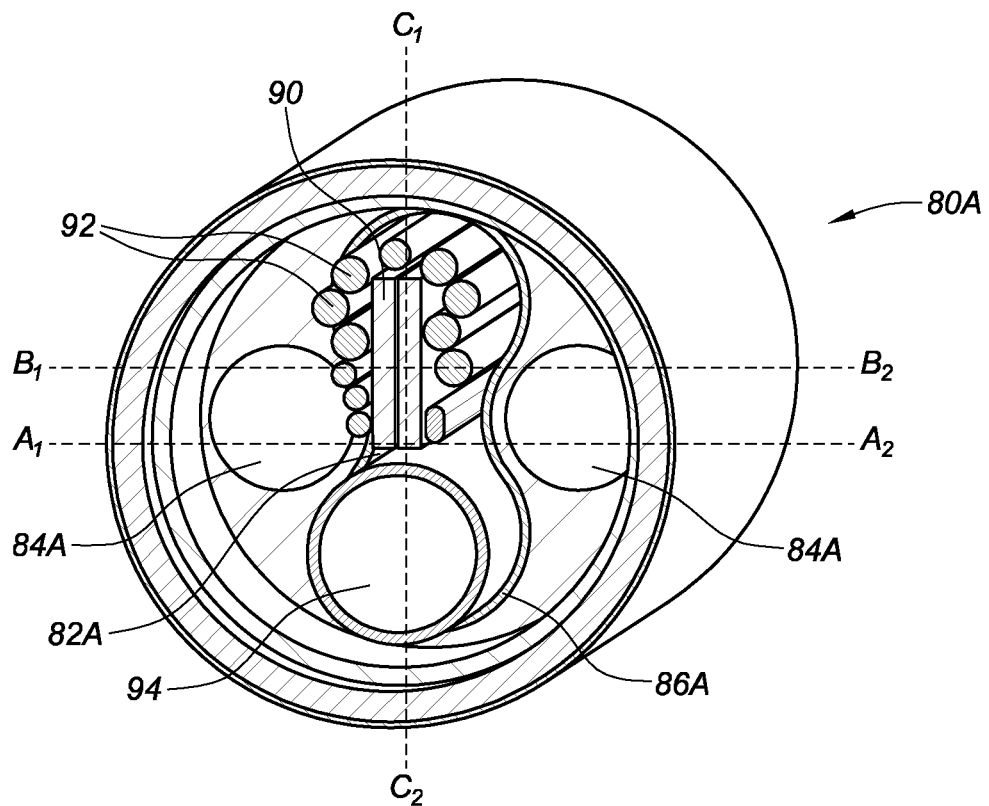
FIG. 6B is an isometric cross-sectional view of the catheter of FIG. 5A comprising a plurality of lumens, including a plurality of wires, in accordance with embodiments of the present disclosure.

FIG. 6B is an isometric cross-sectional view of the catheter of FIG. 6A comprising a plurality of lumens, including a plurality of wires, in accordance with embodiments of the present disclosure. The catheter 80A can also have a stiffening plane represented by the line $C_1$-$C_2$. The shape of one or more of the elements within the first lumen 82A (e.g., the flexible circuit 90 can be configured to resist bending along the stiffening plane $C_1$-$C_2$. The resistance to bending can come from, for example, the shape and/or structure of the elements and the materials used in the elements. Similar to the bending support described above, the resistance to bending along the stiffening plane $C_1$-$C_2$ can also promote and/or assist the catheter 80A in bending along the bending plane $A_1$-$A_2$. For example, when deflected by a user (e.g., using pull wires or other similar mechanisms) the catheter 80A can be disposed to preferentially bend along the bending plane $A_1$-$A_2$ and not bend/minimally bend along the stiffening plane $C_1$-$C_2$.

Figure 7A:
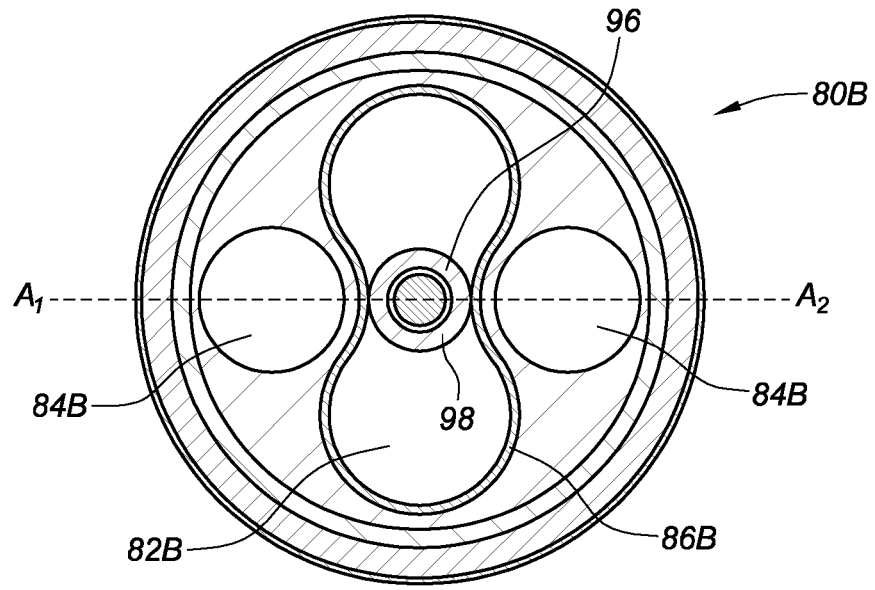
FIG. 7A is a cross-sectional view of a catheter with a plurality of lumens, including a an activation wire, in accordance with embodiments of the present disclosure.

FIG. 7A is a cross-sectional view of a catheter with a plurality of lumens, including a an activation wire, in accordance with embodiments of the present disclosure. A catheter 80B can comprise a first lumen 82B, a lumen liner 86B, an activation wire 96, a compression coil 98, and a plurality of second lumens 84B.

The compression coil 98 can prevent compression of a deflectable section of the distal end portion of the catheter 80B. The compression coil 98 can also ensure that motion from the activation wire 96 transmits to the desired section of the catheter (e.g., a variable loop section in the deflectable section of the distal end portion of the catheter 80B). The activation wire 96 can be used to vary the loop size/curve radius of the deflectable portion of the distal end portion of the catheter 80B. The activation wire 96 can also facilitate motion (i.e., building a second catheter into the primary device such as secondary motion).

Figure 7B:
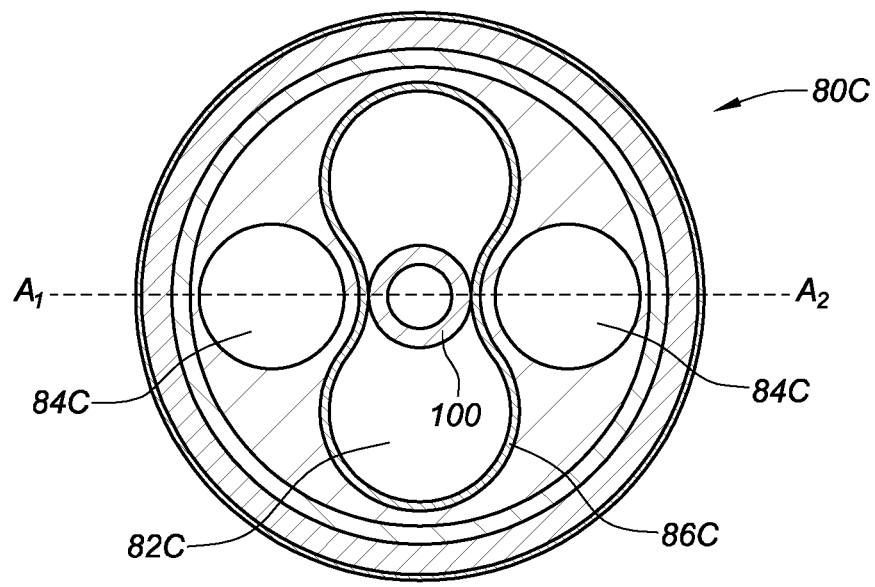
FIG. 7B is an isometric view of the catheter of FIG. 7A comprising a plurality of lumens, in accordance with embodiments of the present disclosure.

FIG. 7B is an isometric view of the catheter of FIG. 7A comprising a plurality of lumens, in accordance with embodiments of the present disclosure. Similar to FIG. 7A, FIG. 7B shows a catheter 80C with a first lumen 82B, a lumen liner 86B, a third lumen 100, and a plurality of second lumens 84C. The third lumen 100 can, in some embodiments, be aligned with a central longitudinal axis of the catheter 80C and can be used, for example, to carry fluids along a length of the catheter 80B (e.g., a closed-loop irrigation return path (e.g., where fluid is supplied though a secondary lumen 94 (shown in FIGS. 6A-B) and removed through the third lumen 100), a secondary irrigation path where the third lumen 100 is used with a second fluid supply (e.g., a fluid source separate from the fluid source 18 shown in FIG. 1), etc.). The third lumen 100 can also be used to supply fluid for applications that require lower flow rates (e.g., compared to those that need a lumen with a larger diameter, such as the secondary lumen 94 in FIGS. 6A-B) and/or to allow for additional space in the lumen liner 86B for other elements. In some embodiments, the third lumen 100 can be used for routing elements from a proximal end portion of the catheter to a distal end portion of the catheter including, for example, a wire (e.g., a high voltage wire), a vacuum, gas/liquid delivery (e.g., for cryotherapy, medicine, etc.), fiber optic fiber(s), a guide wire, a catheter, an endoscope, OCT fiber, or other similar devices that a user may need to use.

Figure 8A:
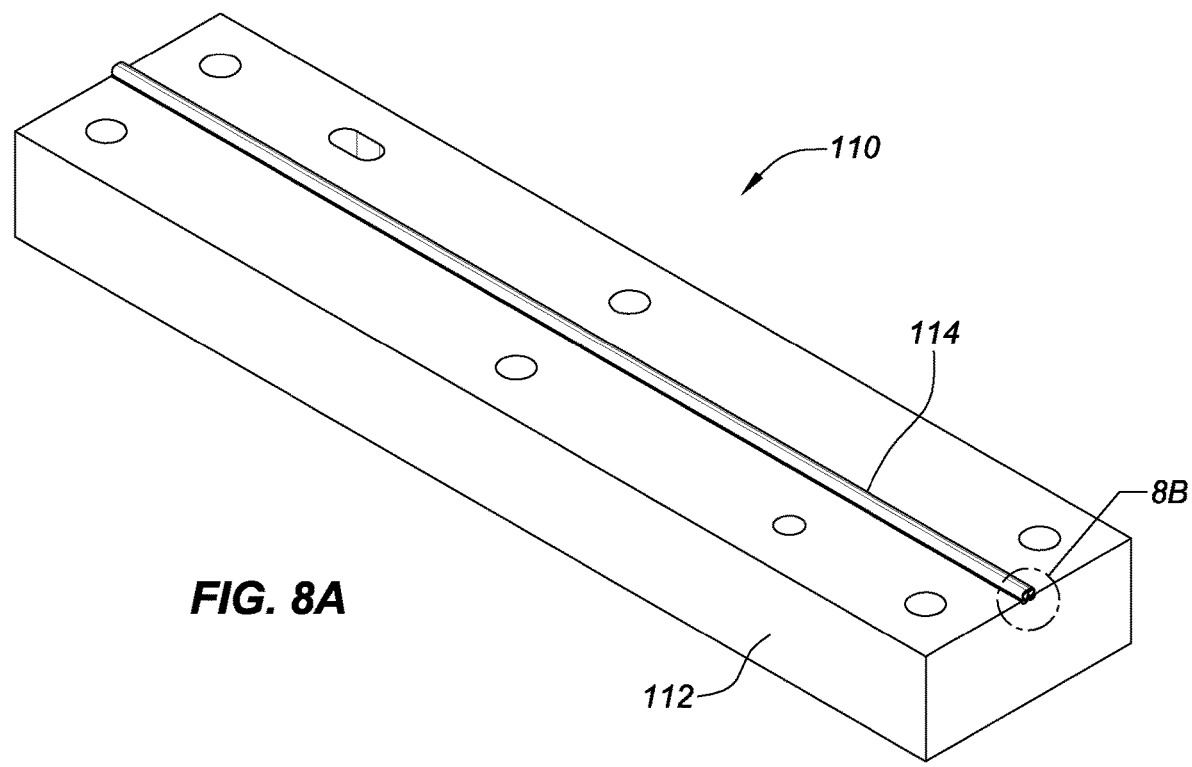
FIGS. 8A-C show various views of a mold for forming a lumen liner, a lumen liner, and mandrels in accordance with embodiments of the present disclosure.
Figure 8B:
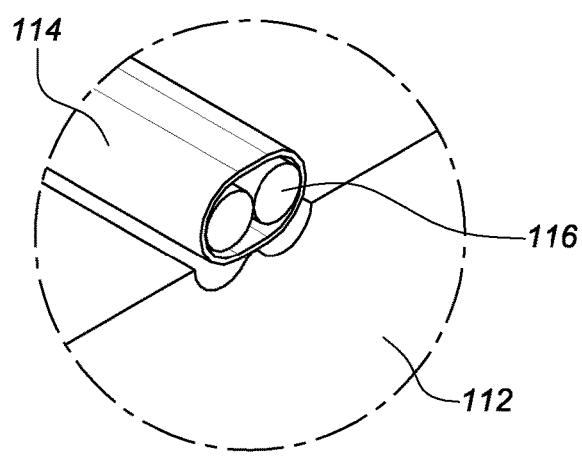
Figure 8C:
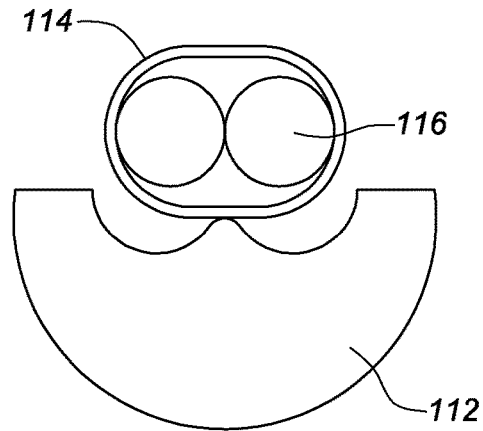

FIGS. 8A-C show various views of a mold for forming a lumen liner, a lumen liner, and mandrels in accordance with embodiments of the present disclosure. FIG. 8A is an isometric view of a mold for forming a lumen liner. A portion of a mold assembly 110 can comprise a first mold form 112 where the mold 110 can be used to form a lumen liner 114. The mold can be any suitable material (e.g., aluminum) can be size to form a desired length and shape of the lumen liner 114. The mold 110 can be configured to be heated and used to compress a material and heat set a specific shape of the lumen liner 114 (e.g., form a shape that corresponds to the cross-sectional shape of the first lumen 82 in FIG. 4).

A method of forming the lumen liner 114 can include the following steps. First, two round mandrels of a suitable material (e.g., a metal) can be inserted into a piece of tubing in a first shape (e.g., round or oval). After insertion, the two mandrels can be in contact with each other and each mandrel can be in contact with a portion of the tubing. Second, the assembly with the tubing and the mandrels can be place into the first mold form 112 and positioned as shown in FIG. 8B. The first mold form 112 can include a profile that corresponds to a portion (e.g., one half) of the cross-sectional shape of the desired lumen liner cross-section.

FIG. 8B is a partial isometric view of the mold for forming the lumen liner from FIG. 8A, in accordance with embodiments of the present disclosure. FIG. 8A shows a closer view of the lumen liner 114, the two mandrels 116 inserted into the lumen liner 114, and the lumen liner 114 and mandrels 116 positioned on the first mold form 112.

FIG. 8C is a partial end view of the lumen liner, the two mandrels of FIGS. 8A-B, in accordance with embodiments of the present disclosure. The two mandrels 116 are in the lumen liner 114, and the lumen liner 114 and mandrels 116 are positioned on the first mold form 112. The lumen liner 114 and mandrels 116 can be centered on the first mold form 112 as shown.

Figure 9A:
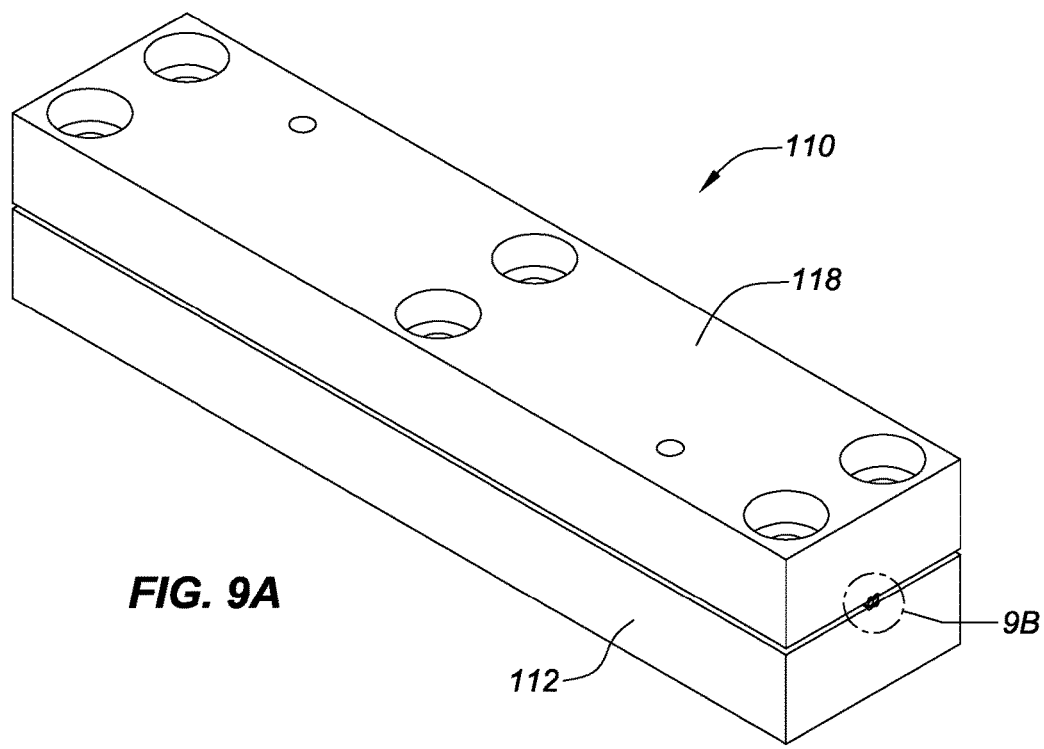
FIGS. 9A-C show various views of a mold assembly, including the first mold of FIG. 8A, in an uncompressed configuration, in accordance with embodiments of the present disclosure.
Figure 9B:
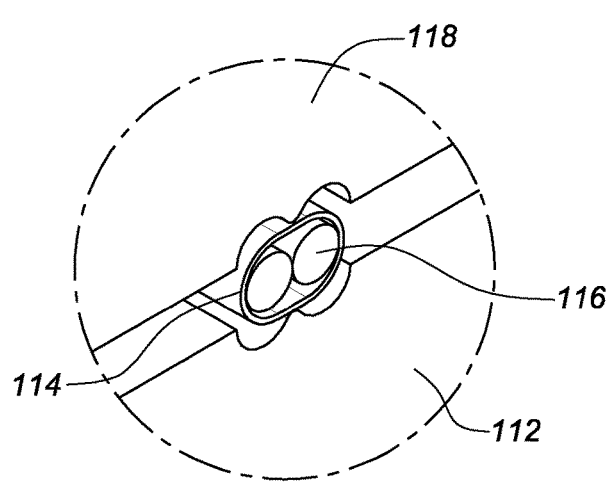
Figure 9C:
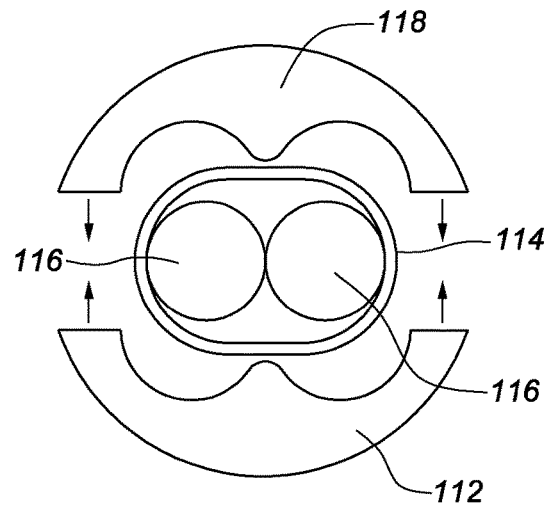

FIGS. 9A-C show various views of a mold assembly, including the first mold of FIG. 8A, in an uncompressed configuration, in accordance with embodiments of the present disclosure. FIG. 9A is an isometric view of the mold assembly 110 comprising the first mold form 112 and a second mold form 118 prior to molding a lumen liner, in accordance with embodiments of the present disclosure. The first mold form 112 and the second mold form 118 can be configured to couple together to facilitate molding (i.e. forming) the lumen liner 114 into a second shape.

FIG. 9B is a partial isometric view of the mold assembly with the lumen liner and mandrels of FIG. 9A prior to molding the lumen liner, in accordance with embodiments of the present disclosure. The mold assembly 110 is positioned with the first mold form 112 and the second mold form 118 prior to molding and the mandrels 116 inside the lumen liner 114.

FIG. 9C is a partial end view of the first mold form, the second mold form, and the lumen liner with the mandrels of FIGS. 9A-B, in accordance with embodiments of the present disclosure. As described herein, the first mold form 112 and the second mold form 118 can be shaped to cause the lumen liner to match the shape of the first mold form 112 and the second mold form 118 when the two mold forms are compressed together (indicated by arrows 120) and heated. A third step in forming a lumen liner 114 include coupling the first mold form 112 and the second mold form 118 and compressing and heating the lumen liner 114 to allow it to take on the shape of the mold. After the mold is cooled and the lumen liner 114 has taken the cross-sectional shape of the first mold form 112 and the second mold form 118, the mold assembly 110 can be opened and the mandrels 116 can be removed from the lumen liner 114, yielding the desired cross-sectional shape (i.e. a second shape).

An additional step can be taken with the lumen liner 114 that adds another layer on an outer surface of the lumen liner 114. A reflowable outer layer (not shown) can be added to the lumen liner 114. The reflowable outer layer can assist with coupling between the lumen liner 114 and the catheter (e.g., the catheter 80A of FIGS. 6A-B).

Figure 10A:
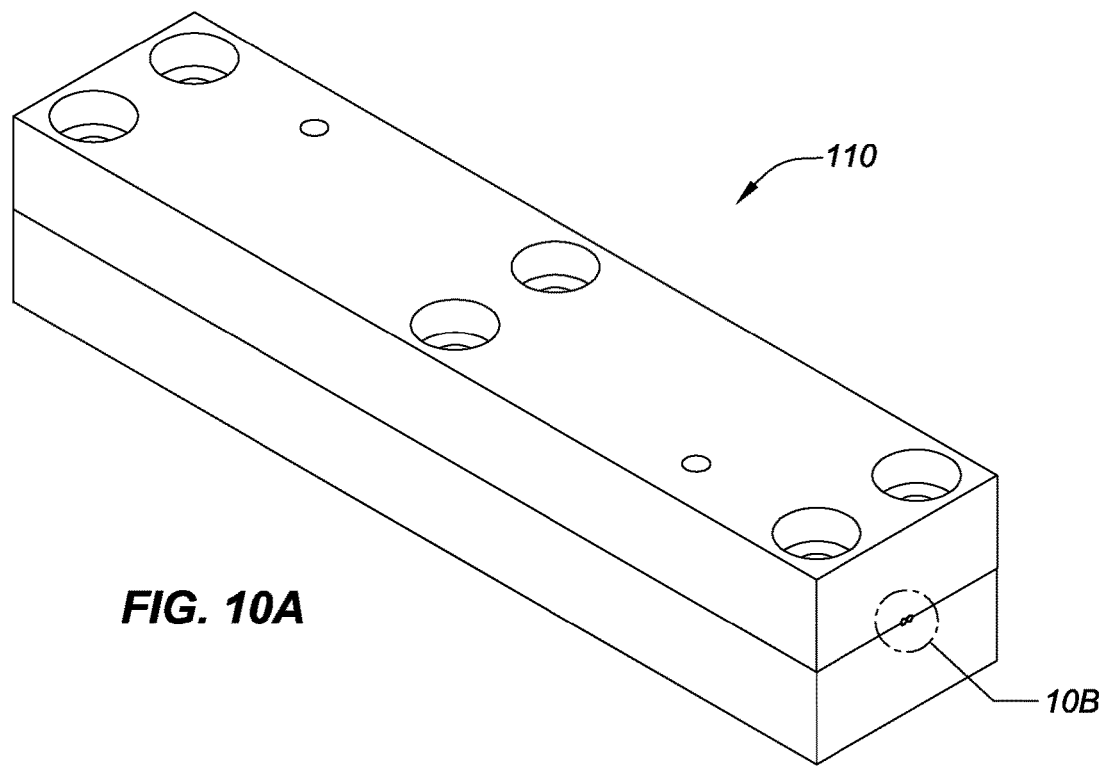
FIGS. 10A-C show various views of the mold assembly of FIGS. 9A-C in a compressed configuration, in accordance with embodiments of the present disclosure.
Figure 10B:
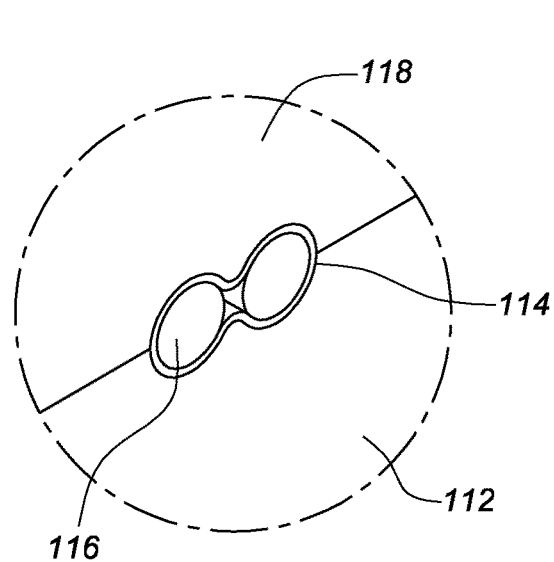
Figure 10C:
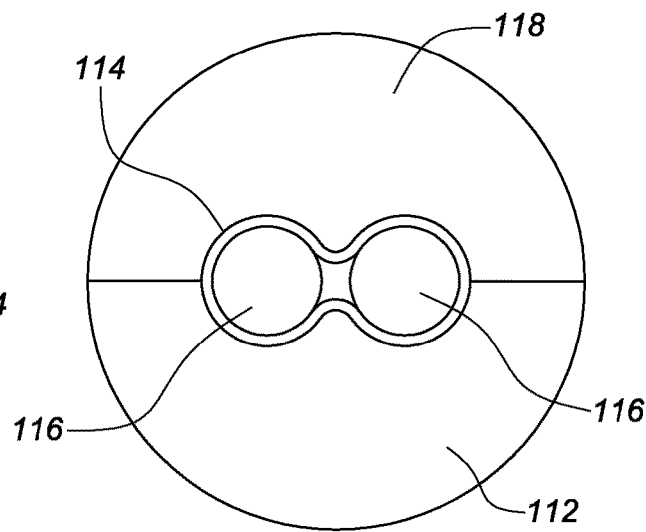

FIGS. 10A-C show various views of the mold assembly of FIGS. 9A-C in a compressed configuration, in accordance with embodiments of the present disclosure. FIG. 10A is an isometric view of the mold assembly of FIG. 9A including the lumen liner and the mandrels after molding, in accordance with embodiments of the present disclosure. A fourth step can be cooling the mold to room temperature to allow the lumen liner 114 to set the shape that conforms to (i.e. matches) the shape of the first mold form 112 and the second mold form 118. After the mold assembly is cooled, the lumen liner 114 will have a cross-sectional shape that corresponds to that of the interior of the mold assembly 110, which can correspond to the interior of a catheter (e.g., the first lumen 82 of the catheter 80 of FIG. 4).

FIG. 10B is a partial isometric view of the first mold form and the second mold form in a compressed configuration with the lumen liner and mandrels, in accordance with embodiments of the present disclosure. As shown in FIG. 10A, the lumen liner 114, after being heated and compressed between the first mold shape 112 and the second mold shape 118, now has a cross-sectional shape that conforms to that of the first mold shape 112 and the second mold shape 118 which can correspond to the interior of a catheter as described herein.

FIG. 10C is a partial end view of the first mold form and the second mold form in a compressed configuration with the lumen liner and mandrels, in accordance with embodiments of the present disclosure. After undergoing the molding process described herein, the lumen liner 114 has a cross-sectional shape that conforms to the shape of the first mold form 112 and the second mold form 118 where the mandrels are separated, creating an additional space (e.g., the additional area 88 of FIG. 5) to create a larger lumen compared to two adjacent circular lumens that are separate (e.g., the plurality of first lumens 62 in FIG. 3).

An alternate method of forming a lumen liner (not shown) can involve using a single mandrel that is shaped to match the desired lumen liner volume. For example, a metal rod (i.e., a metallic structure) can be shaped to match the cross-sectional shape of the lumen liner 82 of FIG. 4. The metallic structure, can then have a polymer (e.g., polyimide) applied to it and then allowed to cool. The application of the polymer can be done using any suitable method (e.g., immersion in a liquid reservoir, deposition, spray, etc.) After that layer of polymer is cool, the metallic structure can be immersed into the liquid polymer and cooled multiple times, where each immersion/cooling cycle adds another layer of polymer. The number of immersions can be controlled to achieve the desired thickness of the lumen liner. After the desired thickness of lumen liner is achieved, the metallic structure can be removed. A benefit of this method would be the potential cost savings by eliminating the secondary heat set forming (i.e. molding) process described above.

Another alternate method for achieving the desired shape of the lumen liner would be to utilize heated circular forming fixtures (not shown) with similar cross sectional shape to the mold assembly 110 discussed herein and shown in FIGS. 8A-10C. The initial lumen liner tube (e.g., round or oval cross-sectional) would be routed thru a series of forming wheels while applying heat and then cooling. This method has the potential to allow a longer section of lumen liner to be formed at one time resulting in faster processing times and lower overall product cost.

Figure 11A:
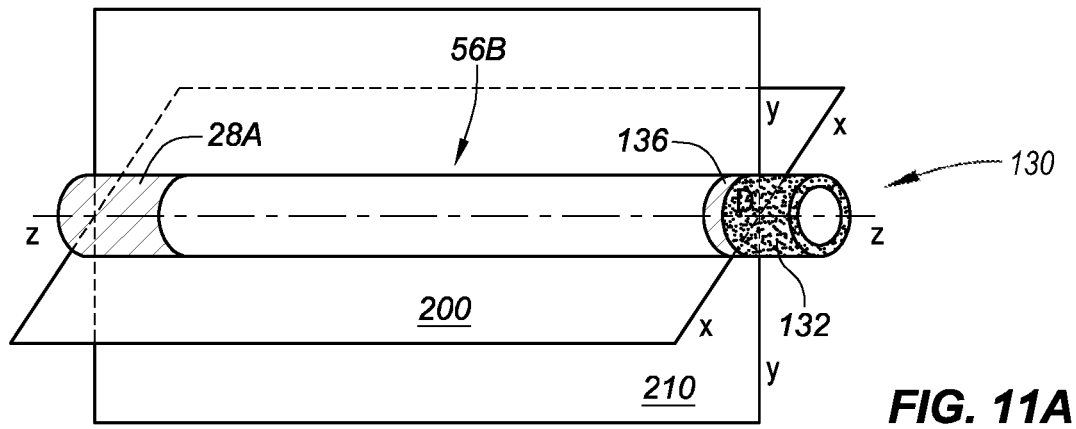
FIGS. 11A-C are isometric views of a deflectable section of a catheter, in accordance with embodiments in the present disclosure.
Figure 11B:
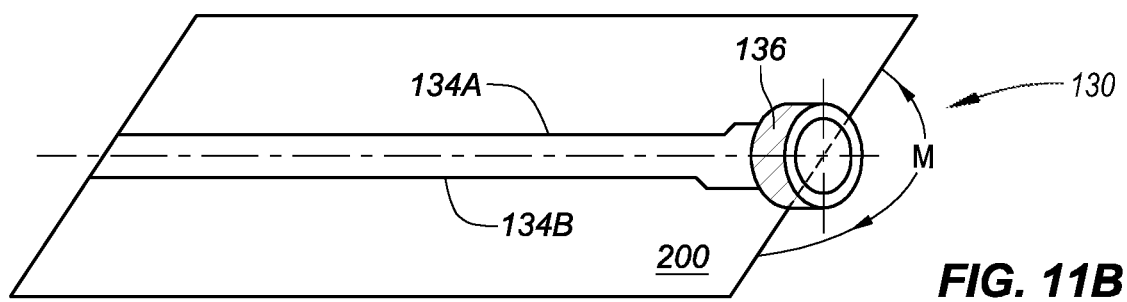
Figure 11C:
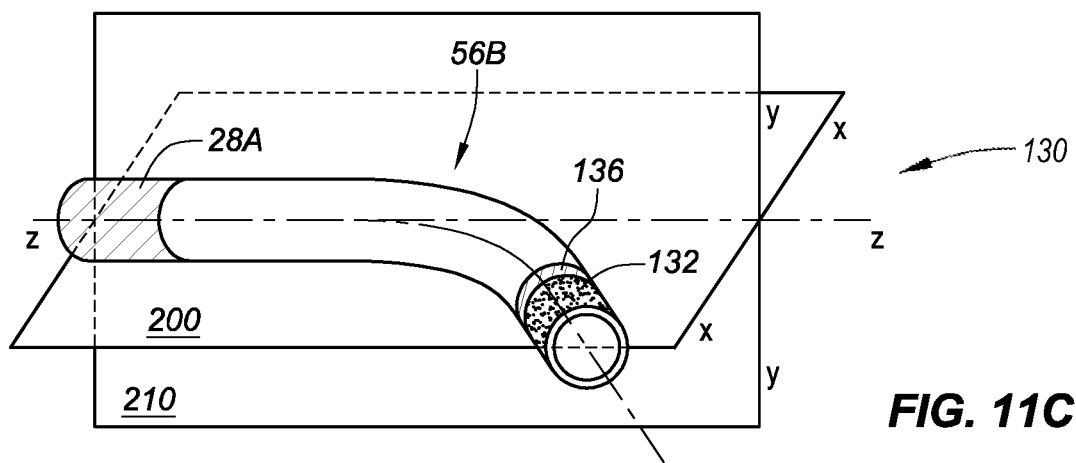

FIGS. 11A-C are isometric views of a deflectable section of a catheter, in accordance with embodiments in the present disclosure. FIG. 11A shows a catheter 130 in a non-deflected state. A distal deflectable catheter shaft portion 56B extends, as a substantially tubular structure, between a distal end of a catheter shaft 28A and, for example, a tip electrode 132. In order to deflect the distal deflectable portion 56B, pull wires 134A and 134B extend from the handle 24/24A (in FIG. 1/FIG. 2) through the shaft 28A (see also, shaft 28 in FIG. 1) and attached to a pull ring 136.

FIG. 11B shows the catheter 130 from FIG. 11A where the deflectable shaft portion, shaft, and electrode are removed for purposes of illustration. Upon deflection by, for example, manipulating the actuator of a handle (e.g., handle 24, FIG. 1 or handle 24A of FIG. 2), the pull wires 134A-B generate eccentric pull forces on the pull ring 136, which imposes a bending moment M on the deflectable catheter shaft portion 56B. As illustrated in FIG. 11C, this deflects a portion of the deflectable catheter shaft portion 56B and thereby allows for disposing the distal tip of the catheter relative to internal areas of interest.

More specifically, as shown in FIG. 11C, the distal tip (e.g., tip electrode 132) of the catheter is caused to move within a bending plane (i.e., sweeping plane) 200. As discussed herein, it can be desirable that the deflection of the distal tip be constrained only within the bending plane 200. Such constraint to the desired bending plane (i.e., to remain planar, to maintain planarity, etc.) may provide consistent and predictable displacement between deflections of the catheter. The position of the pull wires 134A-B can cause the distal tip of the catheter to move within the bending plane 200.

To ensure the sweeping planarity and consistency of the distal deflectable catheter shaft portion, the pull wires must be in near perfect alignment with the designated sweeping plan 200 as shown FIG. 11B. As described above, various elements of the catheter can also allow for bending along the sweeping plane 200 (e.g., the flexible circuits 90 of FIGS. 6A-6B.

As shown in FIG. 11C, the plane 210 is perpendicular to the sweeping plane 200. The physical configuration of the catheter can be such that it resists bending in the direction of the plane 200. For example, the pull wires 134 A-B can, as described above, be aligned with the sweeping plane 200 and the flexible circuits 90 (of FIGS. 6A-B) can be aligned to bend along the sweeping plane 200 and to resist bending along the plane 210 due to the shape/cross-section of the flexible circuits (see discussion above).

Additional information regarding bend planes and planarity of the deflectable section of a distal end of a catheter can be found in U.S. Pat. No. 7,985,215, assigned to St. Jude Medical Atrial Fibrillation Division, filed on Jul. 26, 2011, which is hereby incorporated by reference in its entirety as though fully set forth herein.

Although at least one embodiment of an apparatus for detecting catheters to introducers has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements and can also include elements that are part of a mixture or similar configuration. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An elongate medical device, comprising:
    a deflectable shaft section comprising a shaft material;
    a handle operable to induce a cross-sectional bending of the deflectable shaft section;
    a first lumen within the deflectable shaft section, wherein a cross-sectional shape of the first lumen comprises a peanut shape, wherein the peanut shape is defined by two circular areas joined by a waist area;
    a first lumen liner comprising a first lumen liner material that surrounds and defines the first lumen, wherein the first lumen liner comprises a first lumen liner material that is stiffer than the shaft material to provide planarity control of the deflectable shaft section during the cross-sectional bending of the deflectable shaft section;
    two second lumens within the deflectable shaft section, wherein the two second lumens are disposed diametrically opposed to one another on opposite sides of the first lumen; and
    an irrigation tube disposed in the first lumen.

2. The elongate medical device of claim 1, wherein the peanut shape is symmetrical.

3. The elongate medical device of claim 1, wherein the peanut shape is asymmetrical.

4. The elongate medical device of claim 1, wherein:
    the waist area is smaller than each of the two circular areas; and
    the elongate medical device further comprises a flexible circuit shaped to couple with a portion of the first lumen liner that defines the waist area to hold the flexible circuit in position.

5. The elongate medical device of claim 1, wherein the first lumen liner material comprises a heat setting polymer and the shaft material comprises a reflowable polymer.

6. The elongate medical device of claim 1, further comprising two pull wires via which the handle is drivingly coupled with the deflectable shaft section, wherein each of the two pull wires is disposed in a respective one of the two second lumens.

7. The elongate medical device of claim 6, wherein each of the two second lumens has a circular cross-section.

8. The elongate medical device of claim 1, wherein:
    the first lumen liner comprises an inner layer and an outer layer that surrounds the inner layer; and
    the inner layer comprises the first lumen liner material.

9. The elongate medical device of claim 8, wherein the outer layer comprises a reflowable material.

10. The elongate medical device of claim 1, further comprising a flexible circuit disposed in the first lumen and aligned with an elongated axis of the first lumen liner to contribute to the planarity control of the deflectable shaft section provided by the first lumen liner during the cross-sectional bending of the deflectable shaft section.

11. An elongate medical device, comprising:
    a deflectable shaft section comprising a shaft material;
    a handle operable to induce a cross-sectional bending of the deflectable shaft section;
    a first lumen within the deflectable shaft section, wherein a cross-sectional shape of the first lumen has a peanut shape, wherein the peanut shape is defined by two circular areas joined by a waist area;

a first lumen liner comprising a first lumen liner material that surrounds and defines the first lumen, wherein the first lumen liner comprises a first lumen liner material that is stiffer than the shaft material, and wherein the cross-sectional shape of the first lumen is oriented so that the first lumen liner has an in-plane bending stiffness and an out-of-plane bending stiffness that is greater than the in-plane bending stiffness to provide planarity control of the deflectable shaft section during the cross-sectional bending of the shaft section;

two pull-wire lumens within the deflectable shaft section and disposed diametrically opposed to one another on opposite sides of the first lumen; and two pull wires via which the handle is drivingly coupled with the deflectable shaft section, wherein each of the two pull wires is disposed in a respective one of the two pull-wire lumens, and wherein the two pull wires are actuatable to induce the cross-sectional bending of the deflectable shaft section.

12. The elongate medical device of claim 11, wherein:
the waist area is smaller than each of the two circular areas; and
the elongate medical device further comprises a flexible circuit shaped to couple with a portion of the first lumen liner that defines the waist area to hold the flexible circuit in position.

13. The elongate medical device of claim 11, wherein:
the first lumen liner comprises an inner layer and an outer layer that surrounds the inner layer; and
the inner layer comprises the first lumen liner material.

14. The elongate medical device of claim 13, wherein the outer layer comprises a reflowable material.

* * * * *